United States Patent [19]

McIntyre et al.

[11] Patent Number: 5,409,470
[45] Date of Patent: Apr. 25, 1995

[54] DILATATION CATHETER AND GUIDEWIRE WITH THREADED TIP CONNECTION

[75] Inventors: Jon T. McIntyre, Lowell; William A. Berthiaume, Hudson, both of Mass.

[73] Assignee: C. R. Bard, Inc., Murray Hill, N.J.

[21] Appl. No.: 58,644

[22] Filed: May 7, 1993

[51] Int. Cl.[6] ............................................. A61M 25/00
[52] U.S. Cl. .................................... 604/283; 604/282; 604/96; 604/99; 604/170; 604/280
[58] Field of Search ................ 604/96, 99, 164, 165, 604/170, 280, 282, 283; 128/651, 658, 772; 606/192, 194

[56] References Cited

U.S. PATENT DOCUMENTS

| | | | |
|---|---|---|---|
| 4,004,588 | 1/1977 | Alexander | 128/241 |
| 4,044,765 | 8/1977 | Kline | 604/164 |
| 4,573,470 | 3/1986 | Samson et al. | 128/344 |
| 4,616,653 | 10/1986 | Samson et al. | 128/344 |
| 4,641,654 | 2/1987 | Samson et al. | 128/344 |
| 4,798,598 | 1/1989 | Bonello et al. | 128/772 |
| 4,846,174 | 7/1989 | Willard et al. | 128/344 |
| 4,932,959 | 6/1990 | Horzewski et al. | 606/194 |
| 5,141,518 | 8/1992 | Hess et al. | 604/99 |
| 5,147,317 | 9/1992 | Shank et al. | 604/164 |
| 5,195,989 | 3/1993 | Euteneuer | 604/96 |
| 5,219,335 | 6/1993 | Willard et al. | 604/164 |
| 5,234,437 | 8/1993 | Sepetka | 128/772 |
| 5,259,393 | 11/1993 | Corso, Jr. et al. | 128/772 |
| 5,267,757 | 12/1993 | Fagan et al. | 604/283 |
| 5,271,415 | 12/1993 | Foerster et al. | 128/772 |

*Primary Examiner*—C. Fred Rosenbaum
*Assistant Examiner*—N. Kent Gring
*Attorney, Agent, or Firm*—Wolf, Greenfield & Sacks

[57] ABSTRACT

A guidewire and catheter are adapted for advancement through tight or tortuous vascular anatomy by providing detachably connectible threaded elements at the distal ends of each of the catheter and guidewire. When threaded together, the combined catheter and guidewire provide enhanced column strength to facilitate pushing the two together through the vascular anatomy. Alternately, the guidewire may be rotated in a manner that draws the catheter in screw-like fashion in a distal direction.

8 Claims, 3 Drawing Sheets

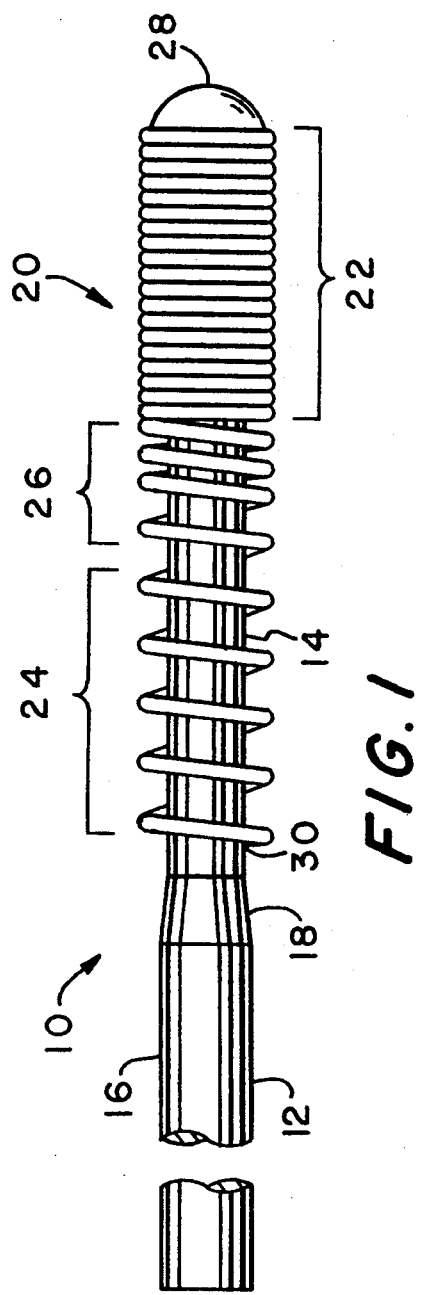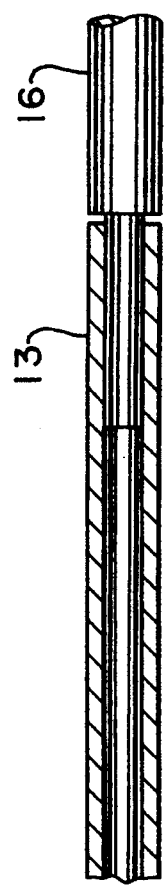

DILATATION CATHETER AND GUIDEWIRE WITH THREADED TIP CONNECTION

FIELD OF THE INVENTION

This invention relates to improvements in dilatation catheters and guidewires.

BACKGROUND OF THE INVENTION

Dilatation catheters are used to dilate various constricted or obstructed regions in the human body. For example, among the more common dilatation procedures is that involving angioplasty, in which a stenosed region of an artery is forcibly dilated by a balloon mounted on the distal end of the catheter. Such arterial stenoses typically are formed by plaque deposited on or in the arterial wall.

A number of types of dilatation catheters are used in angioplasty procedures. Among the most common is that referred to as an over-the-wire catheter, in which the catheter is used together with a guidewire. The guidewire is steerable and of a small diameter (such as disclosed in U.S. Pat. No. 4,545,390 to Leary) so that it can be navigated and advanced through the branches and curves of the patient's artery to the site of the stenosis. The guidewire specifically is advanced through the stenosis, thereby providing a path through the patient's arteries by which the catheter can be guided directly to the stenosis. Once the guidewire is placed, the over-the-wire catheter, which has a lumen receptive to the guidewire, is advanced along the guidewire to the site of the stenosis. The guidewire is pushed along the guidewire to locate its dilatation balloon (in collapsed low profile configuration) into the stenosis. The balloon so positioned, then is inflated with a liquid under pressure and for a duration sufficient to affect the dilatation of the stenosis.

Among the difficulties encountered in balloon dilatation of strictures in body lumens, such as dilatation of stenoses in angioplasty, is that the stenosis may be too narrow to enable the balloon portion of the dilatation catheter to be inserted into the stenosis. That is the result, in part, of the construction of the shaft of the catheter which necessarily is flexible so that it can be advanced along the various curves of the patient's vascular anatomy. Consequently, the column strength of the catheter may not be sufficient to enable the catheter to be pushed through the stenosis. Under those circumstances, other approaches may be required in order to treat the stenosis. Typically, the other approaches may involve the use of another catheter having a smaller profile that may be used to predilate the stenosis to enlarge the opening sufficiently to enable the larger, conventional size dilatation catheter to be inserted into the stenosis. For example, such devices are described in U.S. Pat. Nos. 5,102,390 and 4,846,174. The use of such devices may add to the duration and complexity of the dilatation procedure.

It is among the general objects to provide a catheter and guidewire combination to enhance the ability to pass the dilatation catheter.

SUMMARY OF THE INVENTION

The invention includes the combination of an over-the-wire catheter and guidewire in which the distal ends of each of the catheter and guidewire includes a threaded connection by which they may be detachably secured to each other. The threaded ends of the guidewire and catheter can be connected or disconnected by rotation of the guidewire relative to the catheter. When the distal ends of the catheter and guidewire are connected, they may be pushed, together, to advance the catheter into a stenosis, the column strength of the catheter being reinforced by that of the guidewire. The guidewire, when detached, may be used in a conventional manner, to be manipulated into a desired arterial branch so that the catheter thereafter may be advanced along the guidewire to that branch.

It is an object of the invention to provide a catheter and guidewire combination having a positive distal connection to enhance the combined column strength of the system.

DESCRIPTION OF THE DRAWINGS

The foregoing and other objects and advantages of the invention will be appreciated more fully from the following further description thereof, with reference to the not-to-scale drawings wherein:

FIG. 1 is an illustration of the distal portion of a guidewire in accordance with the invention;

FIG. 1A is an illustration of the proximal end of a guidewire having a means to enable the guidewire to be extended;

DESCRIPTION OF THE PREFERRED EMBODIMENT

Figure 2:
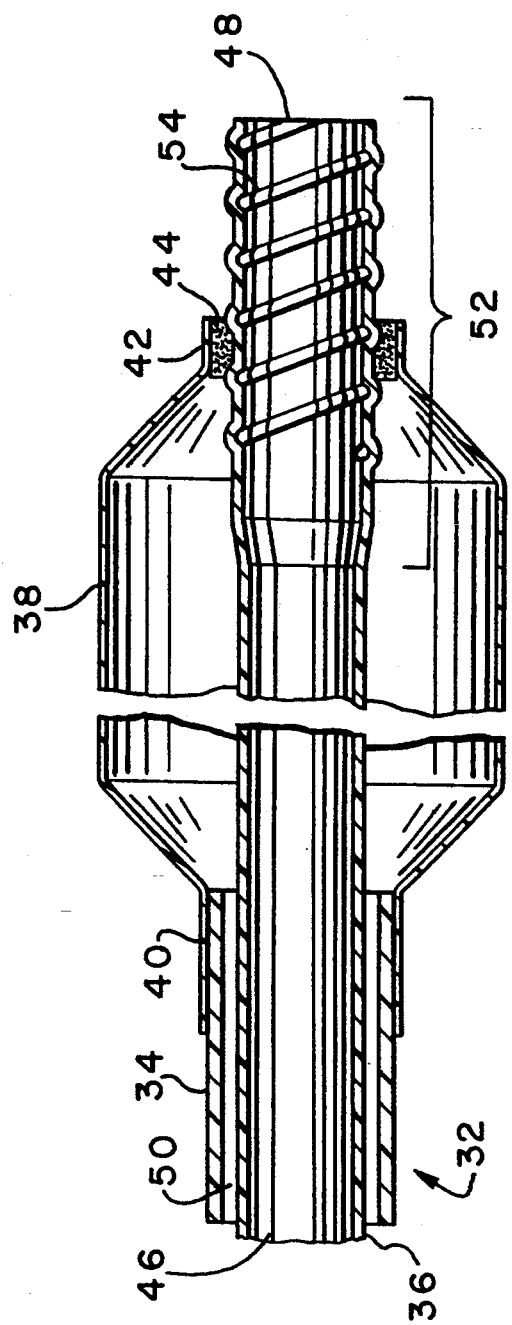
FIG. 2 is a sectional illustration of the distal portion of a balloon dilatation catheter in accordance with the invention and adapted for use with the guidewire of FIG. 1.

FIG. 1 illustrates the distal end of a guidewire embodying the invention. The guidewire 10 has a core wire 12 that extends the full length of the guidewire. The guidewire preferably is of the small diameter steerable type adapted for use in angioplasty such as, for example,, the type of guidewire disclosed in U.S. Pat. No. 4,545,390 (Leary) modified, as described herein, to incorporate the principles of the present invention. The guidewire may be provided, at its proximal end (shown in FIG. 1A) with a connector element 13 by which the proximal end of the guidewire may be connected to the distal end of an extension wire, thereby to facilitate a catheter exchange. Such extendable guidewires are disclosed, for example, in U.S. Pat. Nos. 4,917,103 and 5,133,364, the disclosures of which are incorporated by reference herein, in their entireties. The core wire is formed to form a plurality of segments, the longest of which extends over the major portion of the guidewire from the proximal end. The distal portion of the core wire typically is reduced in diameter to provide increased flexibility so that it is able to pass through narrow tortuous arteries, such as the coronary arteries. The tapering may be progressive and continuous or may be accomplished in steps with cylindrical barrel segments being alternated with shorter tapering segments. In the illustrative embodiment of the present invention, only the distal portion of the guidewire is illustrated including the most distal barrel (constant diameter) segment 14. The most distal segment 14 is connected to a next proximal barrel segment 16 by a connective tapered segment 18. By way of example, for a guidewire having an outer diameter of 0.010 inches along the major proximal portion of its length, the most distal barrel segment 14 may have a diameter of 0.007 inches.

A helical coil 20 is mounted on the distal end of the core wire 12 about the distal segment 14. The helical coil may be formed from stainless steel wire 0.003 inches diameter or from other more radiopaque material, such as platinum, tungsten alloys, gold alloys, or applying such radiopaque platings to the wire as has been described in the art. The coil 20 is formed to include a distal segment 22 and a proximal segment 24. The turns of the coil in the distal segment 22 lie closely adjacent each other. The individual coils in the proximal segment 24 are spaced to a predetermined pitch. As will be described, the proximal segment 24 is intended to serve as a thread-like member by which the distal end of the guidewire may be securely connected to the distal end of the catheter. A transition portion 26 of the coil 20 is defined between the distal and proximal portions 22, 24 in which the pitch may be increased gradually from the closed coil configuration of the distal segment 22 to the widely pitched configuration of the proximal segment 24. The coil is attached at its distal end to the distal end of the core wire segment 14 by a generally hemispherical tip weld 28 as is well-known in the art. The proximal end of the coil 24 also is attached to the distal sequent 14 as by a solder or adhesive joint 30. By way of further dimensional example, in the 0.010 inch diameter guidewire, described above, the outer diameter of the coil 20 may be 0.014 inches. The overall length of the helical coil 20 preferably is at least 4 cm with the proximal segment 24 extending over at least 1 cm. The pitch between adjacent individual coils in the proximal segment 24 preferably is about 0.040 inches.

FIG. 2 illustrates, somewhat diagrammatically, the distal portion of a balloon dilatation catheter in accordance with the invention and adapted to be used with the guidewire illustrated in FIG. 1. The catheter includes an elongate flexible shaft 32 having a proximal end (not shown) and a distal end. The shaft may be formed in a variety of configurations, including the coaxial configuration shown or a configuration in which the lumens are formed in a single extruded tube in a side-by-side arrangement, as is well-known in the art. In the coaxial embodiment illustrated, the catheter shaft may include an outer tube 34 and an inner tube 36. The inner tube 36 may be formed from a suitable polymeric material such as high density polyethylene. The outer tube 34 may be formed from a polyethylene of a lower density than that of the inner tube. The inner tube which may be a single tube or may be formed of segments connected end-to end, extends the full length of the catheter. The distal end of the outer tube 34 terminates short of the distal end of the inner tube 36. A dilatation balloon 38 may be formed from a number of materials such as polyethylene terephlate. The balloon may be made in the manner described in U.S. Pat. No. 4,490,421 (Levy), the disclosure of which is incorporated by reference herein in its entirety. The balloon 38 is formed to include a proximal neck 40 and a distal neck 42. The proximal neck 40 is attached by a suitable adhesive such as to the distal end of the outer tube 34. An ultra-violet curable cyanoacrylate adhesive available from Loctite Corporation under the designation UV350 has been found suitable for such attachments. The distal neck 42 is securely attached to the distal portion of the inner tube 36. A spacer element 44, which may itself be adhesive, may be interposed between the distal neck 42 and the inner tube 36.

A central lumen 46 extends through tube 36 and is open at the distal tip 48 of the inner tube 36. Central lumen 46 is dimensioned and adapted to slidably receive a guidewire, particularly a guidewire having the tip configuration disclosed in FIG. 1. The lumen 46 then is greater in diameter than the maximum diameter of the core wire 12. The diameters of the inner and outer tubes 36, 34 are such that an annular space is defined between the tubes. The annular space 50 is in communication with the interior of the balloon and serves as a lumen by which the balloon may be inflated and deflated. The proximal end of the catheter shaft includes a bifurcation from which separate tubes extend, the separate tubes each communicating with one of the guidewire lumen 46 and inflation lumen 50. Appropriate fittings may be formed on the ends of the proximal tubes for connection with suitable devices such as an inflation/deflation device and the like. The construction of the proximal end of such catheters is well-known to those skilled in the art.

The distal portion of the inner tube 36, in the region of the balloon may be formed from a separate tip tube, is provided with a slightly enlarged diameter distal segment 52 that is formed to include a number of internal female threads 54. The threads 54 are configured and dimensioned to be mateable with the widely pitched proximal segment 24 of the helical coil 20. Thus, in the illustrative embodiment, the inner diameter of the distal segment, may be slightly less than 0.014 inches, the diameter defined by the female threads 54 being adapted to threadably engage the coil turns at the proximal end of the coil. The more proximal portion of the intermediate tube may be of smaller diameter adapted to receive the guidewire. The threads 54 may be formed by molding the distal portion of the inner tube 36 about a forming mandrel having counterpart male threads about its external surface. The mandrel may be inserted into the tip region of the tube 36 which, in turn, may be inserted into a tube of heat shrinkable film. Heat then may be applied to the overlapping regions to cause the film to shrink about the distal portion of the tube 36. Thus, the distal portion of the tube 30 is caused to be constricted about the threaded mandrel while being heated. The assembly then is permitted to cool to enable the distal segment 52 to take permanently the threaded shape. The heat shrinkable film then may be stripped away and the mandrel removed. It should be noted that the distal tip portion of the inner tube may be formed by a separate tip tube that is attached to the distal tip of a somewhat shortened inner tube 36. The use of such a tip tube construction may facilitate manufacture of the threaded portion at the distal end of the catheter. Such a tip tube construction is illustrated, for example, in U.S. application Ser. No. 927,239 filed Nov. 4, 1986 (published as U.S. Pat. No. 4,748,981, Jun. 7, 1988), the disclosure of which is incorporated by reference herein in its entirety.

Figure 3:
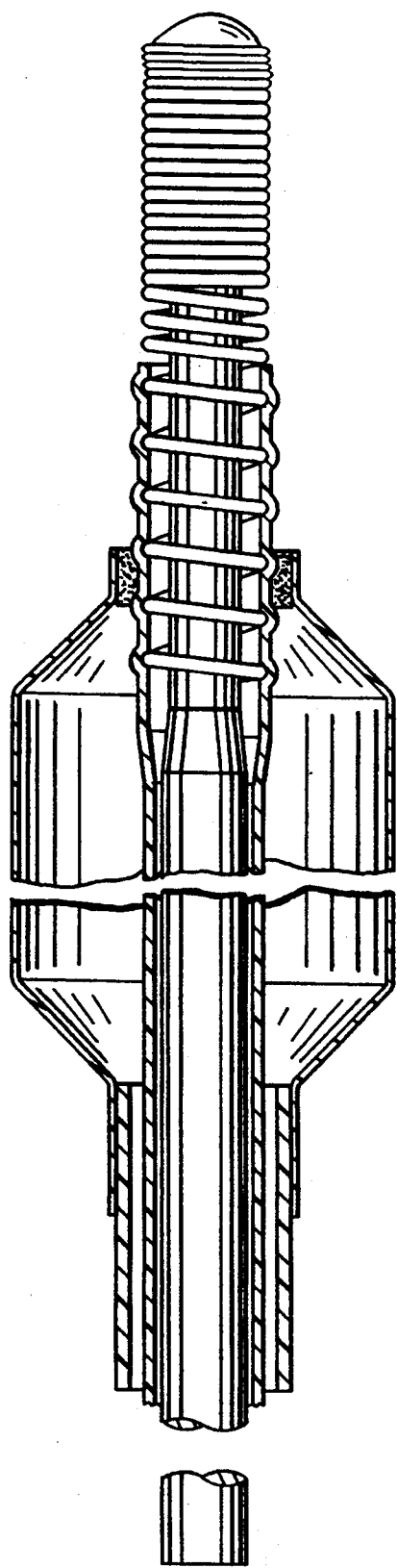
FIG. 3 is an illustration of the distal portions of the guidewire and catheter of FIGS. 1 and 2 when connected.
Figure 4:
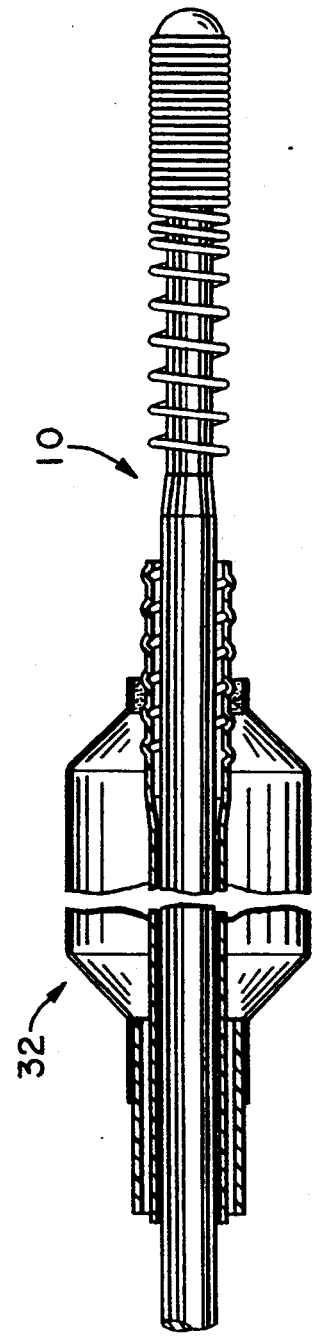
FIG. 4 is a somewhat reduced size illustration of the distal portions of the guidewire and catheter with the guidewire disconnected from the catheter and with the distal tip of the guidewire and with the distal portion of the guidewire projecting distally of the distal end of the catheter.

FIGS. 3 and 4 illustrate the distal end of the device when the catheter and guidewire are combined. In FIG. 3, the guidewire is illustrated as being in threaded engagement with the threaded segment 52 of the catheter.

FIG. 4 illustrates their configuration patient's when the guidewire and catheter are unthreaded and with the guidewire extending distally of and with its coil out of engagement with the catheter. It is contemplated that the catheter and guidewire will be used in a connected configuration when a tight, difficult-to-cross stenosis is anticipated or has been encountered. In either case, the catheter and guidewire are initially assembled by passing the distal end of the catheter over the shaft of the guidewire. The catheter and guidewire need not be threaded together before advancement into the patient, although they may be so connected if desired.

The physician will navigate the combined catheter and guidewire through the patient's arteries. When used in the performance of coronary angioplasty, the catheter and guidewire typically will be advanced together through a guide catheter extending from a percutaneous puncture site in the femoral artery through the aorta and to the ostium of the right or left coronary artery. With the combination so advanced, the guidewire, being detached from the catheter, then can be manipulated and advanced through the coronary arteries to the intended site of treatment. The catheter then is advanced over the guidewire toward the stenosis. Preferably, the guidewire will have been placed so that the distal segment 22 extends through the stenosis while the proximal, widely pitched portion 24 is disposed proximally of the stenosis. The catheter then is advanced while the guidewire is rotated in a direction that causes the thread-like pitched coils on the proximal segment 24 to engage the female threads 54. The two thus are threaded together. So connected, it will be appreciated that a distally directed pushing force on the guidewire will be transmitted to the distal end of the catheter and will act as a force tending to pull the catheter in a distal direction. The connected catheter and guidewire thereby provide, in combination, improved ability to advance the catheter through a tight stenosis and/or tortuous arterial anatomy. The column strength of the combination is substantially greater than that of the catheter alone. At any time during the procedure, the guidewire and catheter may be detached by rotating the guidewire in the reverse direction. When separated, the guidewire may be manipulated independently of the catheter so that it may be guided and navigated to other arterial regions as desired. Additionally, should it be desired to resume dilatation with another catheter, a catheter exchange may be provided by attaching an extension wire to the proximal end of the guidewire and then performing a catheter exchange as described, for example, in U.S. Pat. Nos. 4,922,923 and 5,133,364, the disclosures of which are incorporated herein by reference in their entirety.

In another mode of operation, the threaded connection may be employed, in some instances, to pull the catheter through a tight stenosis or tortuous anatomy by locating the guidewire in a position so that part of the pitched proximal coil segment 24 is within. the stenosis or tortuous segment and a proximal portion of the segment 24 is disposed proximally of that anatomy. The distal end of the catheter then may be brought into engagement with the most proximal turn of the coil and the guidewire then may be rotated in a direction to screw the two together. By maintaining the position of the guidewire while rotating it, the catheter will be threaded onto the coil, thereby drawing the catheter gradually in a distal direction. In some instances, it may be desirable to use this gradual mode of catheter advancement.

From the foregoing, it will be appreciated that the invention provides a new and improved means of advancing a catheter through tight or tortuous blood vessels. The guidewire and catheter combination provides for enhanced column strength when the catheter and guidewire are pushed in unison and provides an alternate mode of operation in which the catheter can be advanced gradually in response to screw-like cooperation between the guidewire and the catheter. It should be understood, however, that the foregoing description of the invention is intended merely to be illustrative thereof and that other embodiments, modifications and equivalents of the invention may be apparent to those skilled in the art without departing from its spirit.

Having thus described the invention what we desire to claim and secure by Letters Patent is:

1. A catheter and guidewire combination comprising:
   an elongate flexible shaft having at least one lumen therein, said lumen being open at the distal end of the shaft;
   the most distal segment of the lumen being formed to define female threads;
   a guidewire having an elongate flexible shaft and a helical coil at its distal end, the guidewire shaft being dimensioned to be received within said lumen;
   the proximal portion of the helical coil including a segment of coiled turns pitched to, threadably engage the female threads on the inner surface of the catheter lumen;
   the coil being attached to the guidewire shaft at the proximal and distal ends of the coil.

2. A catheter and guidewire combination as defined in claim 1 wherein the female thread extends fully to the opening at the distal end of the catheter lumen.

3. A catheter and guidewire combination as defined in either of claims 1 or 2 further comprising the helical coil of the guidewire having a distal segment in which the coil turns are located closely adjacent each other.

4. A catheter and guidewire combination as defined in claim 1 further comprising highly radiopaque means at the distal portion of the guidewire for enabling radiographic visualization of the guidewire.

5. A catheter and guidewire combination as defined in claim 1 further comprising:
   means at the proximal end of the guidewire for connection to an extension wire thereby to facilitate a catheter exchange over said guidewire.

6. A catheter comprising:
   an elongate flexible shaft having at least one lumen therein, the lumen being open and terminating in an orifice at the distal end of the shaft, the lumen being receptive to a guidewire;
   the most distal segment of the lumen being formed to define female threads that extend to the orifice; and
   a balloon mounted to the distal end of the catheter shaft and an inflation lumen extending through the shaft and being in communication with the interior of the balloon.

7. A method for advancing a catheter through a tight stenosis comprising:
   providing a catheter having a connector element at its distal end;
   providing a catheter having a connector element at its distal end, the connector elements of the guidewire and catheter being detachably connectible with each other;

inserting both the guidewire and the catheter into the patient;

effecting connection of the distal ends of the guidewire and the catheter by securely locking them together and while so connected, simultaneously advancing the combined catheter and guidewire through the vascular anatomy;

said step of securely locking the distal ends of the guidewire and catheter comprising threading the distal ends of the guidewire and catheter together.

8. A method for advancing a catheter thorough a tight stenosis or tortuous vascular anatomy comprising:

providing a catheter having a connector element at its distal end;

providing a guidewire having a connector element at its distal end, the connector elements of the guidewire and catheter being detachably connectible with each other;

inserting both the guidewire and the catheter into the vascular anatomy;

threadably connecting the distal ends of the guidewire and catheter;

thereafter maintaining the longitudinal position of the guidewire while rotating the guidewire in a direction to cause the threaded connector at the distal end of the catheter to be drawn onto the threaded portion of the guidewire in a distal direction, thereby to advance the catheter distally in response to rotation of the guidewire.

* * * * *